US008030002B2

(12) United States Patent
Fallon

(10) Patent No.: US 8,030,002 B2
(45) Date of Patent: Oct. 4, 2011

(54) METHODS FOR DIAGNOSING PERVASIVE DEVELOPMENT DISORDERS, DYSAUTONOMIA AND OTHER NEUROLOGICAL CONDITIONS

(75) Inventor: Joan M. Fallon, Yonkers, NY (US)

(73) Assignee: Curemark LLC, Rye, NY (US)

( * ) Notice: Subject to any disclaimer, the term of this patent is extended or adjusted under 35 U.S.C. 154(b) by 0 days.

(21) Appl. No.: 09/990,909

(22) Filed: Nov. 16, 2001

(65) Prior Publication Data

US 2002/0081628 A1 Jun. 27, 2002

Related U.S. Application Data

(60) Provisional application No. 60/249,239, filed on Nov. 16, 2000.

(51) Int. Cl.
  *G01N 33/53* (2006.01)
  *G01N 33/554* (2006.01)
  *G01N 33/573* (2006.01)
  *C12Q 1/02* (2006.01)

(52) U.S. Cl. ......... 435/7.1; 435/7.2; 435/7.32; 435/7.4; 435/29

(58) Field of Classification Search ............ 435/34, 435/38, 5, 6, 9.1, 7.2, 7.22, 7.32, 7.35, 7.37, 435/7.4, 7.92, 7.93, 794, 91.1, 91.2, 4, 8, 435/183, 243; 436/514, 547, 548, 63, 86, 436/87; 422/56, 58, 261; 530/349, 350, 530/413, 300; 536/23.1, 24, 32; 514/2
See application file for complete search history.

(56) References Cited

U.S. PATENT DOCUMENTS

| | | | |
|---|---|---|---|
| 3,002,883 A | 10/1961 | Butt et al. | |
| 3,223,594 A | 12/1965 | Hoek et al. | |
| 3,357,894 A | 12/1967 | Uriel et al. | |
| 3,515,642 A | 6/1970 | Mima et al. | |
| 3,574,819 A | 4/1971 | Gross et al. | |
| 3,940,478 A | 2/1976 | Kurtz | |
| 4,079,125 A | 3/1978 | Sipos | |
| 4,145,410 A | 3/1979 | Sears | |
| 4,241,046 A | 12/1980 | Papahadjopoulos et al. | |
| 4,826,679 A | 5/1989 | Roy | |
| 5,190,775 A | 3/1993 | Klose | |
| 5,250,418 A | 10/1993 | Moller et al. | |
| 5,324,514 A | 6/1994 | Sipos | |
| 5,436,319 A * | 7/1995 | Kung et al. .................. 530/350 |
| 5,437,319 A | 8/1995 | Garuglieri | |
| 5,439,935 A | 8/1995 | Rawlings et al. | |
| 5,460,812 A | 10/1995 | Sipos | |
| 5,476,661 A | 12/1995 | Pillai et al. | |
| 5,527,678 A * | 6/1996 | Blaser et al. .................. 435/6 |
| 5,585,115 A | 12/1996 | Sherwood et al. | |
| 5,607,863 A * | 3/1997 | Chandler ..................... 422/104 |
| 5,648,335 A | 7/1997 | Lewis et al. | |
| 5,674,532 A | 10/1997 | Atzl et al. | |
| 5,686,311 A | 11/1997 | Shaw | |
| 5,750,104 A | 5/1998 | Sipos | |
| 5,776,917 A | 7/1998 | Blank et al. | |
| 5,858,758 A | 1/1999 | Hillman et al. | |
| 5,952,178 A * | 9/1999 | Lapidus et al. .................. 435/6 |
| 5,958,875 A | 9/1999 | Longo et al. | |
| 5,985,891 A | 11/1999 | Rowe | |
| 6,011,001 A | 1/2000 | Navia et al. | |
| 6,013,286 A | 1/2000 | Klose | |
| 6,020,310 A * | 2/2000 | Beck et al. .................. 424/198.1 |
| 6,020,314 A | 2/2000 | McMichael | |
| 6,153,236 A | 11/2000 | Wu et al. | |
| 6,187,309 B1 * | 2/2001 | McMichael et al. ....... 424/159.1 |
| 6,197,746 B1 | 3/2001 | Beck et al. | |
| 6,210,950 B1 * | 4/2001 | Johnson et al. ............. 435/252.3 |
| 6,251,478 B1 | 6/2001 | Pacifico et al. | |
| 6,261,613 B1 | 7/2001 | Narayanaswamy et al. | |
| 6,280,726 B1 | 8/2001 | Weinrauch et al. | |
| 6,309,669 B1 | 10/2001 | Setterstrom et al. | |
| 6,399,101 B1 | 6/2002 | Frontanes et al. | |
| 6,482,839 B1 * | 11/2002 | Thornfeldt ..................... 514/345 |
| 6,534,063 B1 | 3/2003 | Fallon | |

(Continued)

FOREIGN PATENT DOCUMENTS

DE 43 32 985 3/1995

(Continued)

OTHER PUBLICATIONS

Parisi et al., "Evaluation of New Rapid Commercial Enzyme Immunoassay for Detection of Cryptosporidium Oocysts in Untreated Stool Specimens," J. Clin. Microbiol., vol. 33(7), pp. 1963-1965 (1995).*

(Continued)

*Primary Examiner* — Albert Navarro
(74) *Attorney, Agent, or Firm* — Wilson Sonsini Goodrich & Rosati

(57) ABSTRACT

Methods for aiding in the diagnosis of disorders including, but not limited to, PDDs (Pervasive Development Disorders), Dysautonomic disorders, Parkinson's disease and SIDS (Sudden Infant Death Syndrome). In one aspect, a diagnosis method comprises analyzing a stool sample of an individual for the presence of a biological marker (or marker compound) comprising one or more pathogens, which provides an indication of whether the individual has, or can develop, a disorder including, but not limited to, a PDD, Dysautonomia, Parkinsons disease and SIDS. Preferably, the presence of one or more pathogens is determined using a stool immunoassay to determine the presence of antigens in a stool sample, wherein such antigens are associated with one or more pathogens including, but not limited to, *Giardia, Cryptosporidium, E. histolytica, C. difficile*, Adenovirus, Rotavirus or *H. pylori*.

44 Claims, 4 Drawing Sheets

U.S. PATENT DOCUMENTS

| | | | |
|---|---|---|---|
| 6,534,259 B1 * | 3/2003 | Wakefield | 435/5 |
| 6,632,429 B1 | 10/2003 | Fallon | |
| 6,660,831 B2 | 12/2003 | Fallon | |
| 6,727,073 B1 * | 4/2004 | Moore et al. | 435/7.32 |
| 6,743,447 B2 | 6/2004 | Labergerie et al. | |
| 6,797,291 B2 | 9/2004 | Richardson | |
| 6,835,397 B2 | 12/2004 | Lee et al. | |
| 6,852,487 B1 * | 2/2005 | Barany et al. | 506/4 |
| 7,101,573 B2 | 9/2006 | Szymczak et al. | |
| 7,129,053 B1 * | 10/2006 | Reiter et al. | 435/7.1 |
| 7,138,123 B2 | 11/2006 | Fallon | |
| 2002/0037284 A1 | 3/2002 | Fallon | |
| 2002/0090653 A1 | 7/2002 | Fallon | |
| 2003/0097122 A1 * | 5/2003 | Ganz et al. | 606/7 |
| 2004/0057944 A1 | 3/2004 | Galle et al. | |
| 2004/0057962 A1 * | 3/2004 | Timmerman | 424/190.1 |
| 2004/0071683 A1 | 4/2004 | Fallon | |
| 2004/0076590 A1 | 4/2004 | Wilkins, Jr. | |
| 2004/0101562 A1 | 5/2004 | Maio | |
| 2004/0121002 A1 | 6/2004 | Lee et al. | |
| 2004/0209790 A1 | 10/2004 | Sava et al. | |
| 2005/0187130 A1 | 8/2005 | Brooker et al. | |
| 2006/0105379 A1 | 5/2006 | Wu et al. | |
| 2006/0182728 A1 | 8/2006 | Fallon | |
| 2006/0183180 A1 | 8/2006 | Fallon | |
| 2006/0198838 A1 | 9/2006 | Fallon | |
| 2006/0259995 A1 | 11/2006 | Cayouette et al. | |
| 2007/0053895 A1 | 3/2007 | Fallon | |
| 2007/0116695 A1 | 5/2007 | Fallon | |
| 2008/0058282 A1 | 3/2008 | Fallon | |
| 2008/0152637 A1 | 6/2008 | Fallon | |
| 2008/0161265 A1 | 7/2008 | Fallon et al. | |
| 2008/0166334 A1 | 7/2008 | Fallon | |
| 2008/0219966 A1 | 9/2008 | Fallon | |
| 2008/0254009 A1 * | 10/2008 | Finegold | 424/93.41 |
| 2008/0279839 A1 | 11/2008 | Schuler et al. | |
| 2008/0317731 A1 | 12/2008 | Gramatikova et al. | |
| 2009/0130081 A1 | 5/2009 | Fallon | |
| 2009/0197289 A1 | 8/2009 | Fallon | |
| 2009/0232789 A1 | 9/2009 | Fallon | |
| 2009/0263372 A1 | 10/2009 | Fallon | |
| 2009/0285790 A1 | 11/2009 | Fallon | |
| 2009/0286270 A1 | 11/2009 | Fallon | |
| 2009/0324572 A1 | 12/2009 | Fallon | |
| 2009/0324730 A1 | 12/2009 | Fallon | |
| 2010/0092447 A1 | 4/2010 | Fallon | |
| 2010/0169409 A1 | 7/2010 | Fallon et al. | |
| 2010/0233218 A1 | 9/2010 | Fallon | |
| 2010/0260857 A1 | 10/2010 | Fallon et al. | |

FOREIGN PATENT DOCUMENTS

| | | | |
|---|---|---|---|
| EP | 0 451 484 | | 10/1991 |
| EP | 0 564 739 | | 1/2000 |
| GB | 2 347 742 | | 9/2000 |
| GB | 2 347 742 A | * | 9/2000 |
| JP | 62-230714 | | 10/1987 |
| WO | WO 95/22344 | | 8/1995 |
| WO | WO 98/22499 | | 5/1998 |
| WO | WO 98/52593 | | 11/1998 |
| WO | WO 99/64059 | | 12/1999 |
| WO | WO 00/09142 | | 2/2000 |
| WO | 01/27612 | * | 4/2001 |
| WO | WO 01/43764 | | 6/2001 |
| WO | WO 02/14537 A2 | | 2/2002 |
| WO | WO 02/14537 A3 | | 5/2002 |
| WO | WO 2009/114757 A2 | | 9/2009 |
| WO | WO 2010/002972 A1 | | 1/2010 |
| WO | WO 2010/080830 A1 | | 7/2010 |
| WO | WO 2010/080835 A1 | | 7/2010 |

OTHER PUBLICATIONS

Dobbs et al., "Link between *Helicobacter pylori* Infection and Idiopathic Parkinsonism," Medical hypothesis, vol. 55(2), pp. 93-98 (2000).*

Tsang et al., "Extragastroduodenal conditions assocaited with *Helicobavter pylori* infection", Hong Kong Medical Journal, vol. 5(2), pp. 169-174 (1999).*

Cruse et al. illustrated Dictionary of Immunology, CRC Press, New York 1995.*

Woodward et al., "Ischaemic enterocolitis complicating idiopathic dysatuonomia," Gut 43: 285-287 (1998).*

Koster et al., "Evidence based medicine and extradigenstive manifestations of *Helicobacter pylori*," Acta Gastro-Enterologica Belgica, vol. 63(4), pp. 388-392 (2000).*

Mesh Browser, "Child Development Disorders, Pervasive," and "Attentiaon Deficit and Disruptive Behavior Disorders," http://www.nlm.nih.gov/mesh/2002/MBrowser.html, National Library of Medicine, 2001.*

Finegold et al., Clinical Infectious Diseases, vol. 35 (Supp 1), pp. S6-15 (2002).*

Filipek et al., "The screening and diagnosis of autistic spectrum disorders.," Journal of autism and developmental disorders, vol. 29 No. 6, pp. 439-484 (Dec. 1999).*

Happe et al., "The neuropsychology of autism.," Brain, vol. 119 No. 4, pp. 1377-1400 (1996).*

Skeels et al, 1990, vol. 80, pp. 305-308, American Journal of Public Health.*

Nevo et al, 1997, The Journal of Infectious Diseases, vol. 176(Suppl2), pp. S154-S156.*

Peters et al 1986, Journal of Clinical Microbiology, vol. 24(4), Oct. 1986, pp. 684-685.*

Garcia et al, 2000, vol. 38(9) Journal of Clinical Microbiology, Sep. 2000, pp. 3337-3340.*

Sandler et al, 2000, Journal of Child Neurology, Jul. 2000, vol. 15(7), pp. 429-435, Short term benefit from Oral Vancomycin Treatment of Regressive-Onset Autism.*

U.S. Appl. No. 09/929,592, filed Aug. 14, 2001 entitled: Methods for Diagnosing and Treating Dysautonomia and Other Dysautonomic Conditions.

U.S. Appl. No. 09/466,559, filed Dec. 17, 1999 entitled: Methods for Treating Pervasive Development Disorders.

U.S. Appl. No. 09/707,395, filed Nov. 7, 2000 entitled: Methods for Treating Pervasive Development Disorders.

"Correlation between protein intake and daily levodopa dosage," Azilect/Rasagiline, Obtained from the Internet May 2, 2007, http://www.azilect.eu/media/cnsnews/showitem.aspx?i=d1c603e4-3c61-4aal-a376-6e519a5a0f80.

"Digestive Enzyme," Retrieved from the internet.<http://en.wikipedia.org/wiki/Digestive_enzyme>. Retrieved on Sep. 10, 2009.

"NINDS Dysautonimia Information Page," Retrieved from the internet on Sep. 10, 2009. http://www.ninds.nih.gov/disorders/dysautonomia/dysautonomia.htm.

"NINDS Guillain-Barre Syndrome Information Page," Retrieved from the internet on Sep. 15, 2009, http://www.ninds.nih.gov/disorders/gbs/gbs.htm.

Adams, "Summary of Defeat Autism Now! (DNN!) Oct. 2001 Converence," Retrieved from the Internet Dec. 18, 2008, http://puterakembara.org/rm/DAN2001.htm.

Axelrod, "Secretin Treatment for Gastrointestinal Dysmobility in Patients with Familial Dysautonomia," New York University School of Medicine, Grant Recipient Awards, Mar.-May 2000, www.med.nyu.edu/ogars/awards/awards 2000/page2.html.

Barlow, "A Comparison of the Blood Pressure, Kidney Volume and the Pancreatic Secretory Response Following the Vein Administration of Various Secretin Preparations," *Am. J. Phys.*, 1927, 81:182-188.

Belmonte and Bourgeron, "Fragile X syndrome and autism at the intersection of genetic and neural networks," *Nat. Neurosci.Neurosci*, 2006, 9(10):1221-1225.

Blackmer, "Parkinson Disease: treatment and Medication," Mar. 10, 2009, Retrieved from the internet. <http://emedicine.medscape.com/article/312519-treatment>. Retrieved on Sep. 15, 2009.

Bode and Bode, "Usefulness of a simple photometric determination of chymotrypsin activity in stools—results of a multicentre study," *Clin Biochem.*, 1986, 19:333-337.

Campbell et al., "A genetic variant that disrupts *MET* transcription is associated with autism," *Proc Natl Acad Sci*, 2006, 103(45):16834-16839.

Carlton, "Autism and Malnutrition: The Milk Connection," Retrieved from the Internet Feb. 18, 2008, http://www.mercola.com/2004/autism_malnutirition.htm.

Darman, "An introduction to Alternative Medicine for Psychiactric Conditions," [online] Oct. 22, 2007, [retrieved on Sep. 18, 2009] retrieved from: http:web.archive.org/web/20071022104238/http://altp [therapies4bipolar.info/ortho/html.

Happe et al., "Time to give up on a single explanation for autism," *Nat. Neurosci.*, 2006, 9(10):1218-1220.

Horvath et al., "Improved Social and Language Skills After Secretion Administration in Patients with Autistic Spectrum Disorders," *Journal of the Association for Academic Minority Physicians*, 1998, 9(1):9-15.

Hoshiko et al., "The Effect of the Gastrointestinal Hormones on Colonic Mucosal Blood Flow," *Acta Medica Nagasakiensia*, 1994, 39(4):125-130.

Kaspar et al., "New Photometric Assay for Chymotrypsin in Stool," *Clinical Chemistry*, 1984, 30(11):1753-1757.

Layer et al., "Pancreatin Enzyme Replacement Therapy," *Current Gastroenterology Reports*, 2001, 3:101-108.

Macready, "Parkinson's Disease Treatment: What You Should Know," Retrieved from the internet. <http://www.everydayhealth.com/parkinsons-disease/parkinsons-disease-treatment-overview.aspx>. Retrieved on Sep. 15, 2009.

Marczewska et al., "Protein intake in Parkinsonian patients using the EPIC food frequency questionnaire," *Mov Disord.*, 2006, 21(8):1229-1231.

"Autism," Merck Manual Online Medical Library Home Addition retrieved from the Internet Mar. 10, 2008, retrieved from http://www.merck.com/mmhge/sec23/ch286/ch286b.html.

Marsh, "Neuropsychiatric Aspects of Parkinson's Disease," *Psychosomatics*, 2000, 41(1):15-23.

mayoclinic.com, "Autism," Retrieved from Internet Mar. 10, 2008, retrieved from http://www/mayoclinic.com/health/autism/DS00348/DSECTION=2.

Mayo Clinic Staff, "Bipolar disorder," [online], Jan. 4, 2008 [retrieved on Sep. 9, 2009], retrieved from: http://www.mayoclinic.com/health/bipolardisorder/DS00356/DSECTION=symptoms.

Mayo Clinic Staff, "Obsessive-compulsive disorder," [online] Dec. 21, 2006 [retrieved on Sep. 18, 2009] retrieved from http://www.preferredalternatives.org/lat/WellnessLibrary/anxiety &PanicDisorders/Obsessive-CompulsiveDisorders/Obsessive-CompulsiveDisorder-Mayoclinic.pdf.

Mayo Clinic Staff, "Oppositional defiant disorder," [online] Dec. 19, 2007 [retrieved on Sep. 18, 2009], retrieved from: http://www.mayoclinic.com/health/oppositional-defiant-disorder/DS00630/DSECTION=symptoms.

Medsafe, Data Sheet for alpha-lactose, Jul. 21, 1999, retrieved from Internet Feb. 28, 2008, retrieved from http://www.medsafe.govt.nz/Profs/Datasheet/a/Alphalactulosesyrup.htm.

Michell et al., "Biomarkers And Parkinson's Disease," *Brain*, 2004, 127(8):1693-1705.

Nachaegari and Bansal, "Coprocessed excipients for solid dosage forms," *Pharmaceutical Technology*, 2004, pp. 52, 54, 56, 58, 60, 62, 64.

Remtulla et al., "Stool Chymotrypsin Activity Measured by a Spectrophotometric Procedure to Identify Pancreatic Disease in Infants," *Clinical Biochemistry*, 1986, 19:341-342.

Rogers, *No more heartburn: Stop the pain in 30 day—Naturally*, 2000, p. 172.

Schiller, "Review Articile: the therapy of constipation," *Aliment Pharmacol Ther.*, 2001, 15:749-763.

Sherwood and Becker, "A new class of high-functionality excipients: Silicified microcrystalline cellulose," *Pharm. Tech.*, 1998, 22(10):78-88.

Seneca and Henderson, "Enhancement of Brain L-Dopa Concentration With A-Chymotrypsin," *J. American Geriatrics Society*, 1973, pp. 256-258.

The Alzheimer's Association, "Basics of Alzheimer's Disease" [online], 2005 [retrieved on Sep. 18, 2009], retrieved from: http://www.alz.org/national/documents/brochure_basicsofalz_low/pdf.

USPTO Office Action in U.S. Appl. No. 09/707,395, mailed Jan. 29, 2002.

USPTO Office Action in U.S. Appl. No. 09/707,395, mailed Aug. 30, 2002, 8 pages.

USPTO Office Action in U.S. Appl. No. 09/466,559, mailed Nov. 26, 2001.

USPTO Office Action in U.S. Appl. No. 09/466,559, mailed May 22, 2002.

USPTO Office Action in U.S. Appl. No. 10/681,018, mailed Jan. 8, 2010, 21 pages.

Fish & Richardson P.C., Amendment in Reply to Final Office Action dated Apr. 28, 2009 in U.S. Appl. No. 10/681,018 filed Oct. 28, 2009, 20 pages.

USPTO Final Office Action in U.S. Appl. No. 10/681,018, mailed Apr. 28, 2009, 8 pages.

Kristina M. Grasso, ESQ. PLLC Amendment in Reply to Action dated Aug. 18, 2008 in U.S. Appl. No. 10/681,018, filed Feb. 7, 2009, 7 pages.

USPTO Office Action in U.S. Appl. No. 10/681,018, mailed Aug. 18, 2008, 6 pages.

Kristina M. Grasso, ESQ. PLLC Response to Advisory Action dated Jun. 3, 2008 in U.S. Appl. No. 10/681,018, filed Jun. 17, 2008, 11 pages.

USPTO Advisory Action in U.S. Appl. No. 10/681,018, mailed Jun. 3, 2008, 4 pages.

Kristina M. Grasso, ESQ. PLLC Amendment in Reply to Action dated Mar. 17, 2008 in U.S. Appl. No. 10/681,018, filed May 19, 2008, 10 pages.

USPTO Final Office Action in U.S. Appl. No. 10/681,018, mailed Mar. 17, 2008, 10 pages.

Kristina M. Grasso, ESQ. PLLC Amendment in Reply to Action dated Aug. 7, 2007 in U.S. Appl. No. 10/681,018, filed Dec. 7, 2007, 11 pages.

USPTO Office Action in U.S. Appl. No. 10/681,018, mailed Aug. 7, 2007, 10 pages.

Maine & Asmus Amendment in Reply to Action dated Dec. 22, 2006 in U.S. Appl. No. 10/681,018, filed May 18, 2007, 11 pages.

USPTO Office Action in U.S. Appl. No. 10/681,018, mailed Dec. 22, 2006, 8 pages.

Maine & Asmus Response to Election/Restriction Requirement dated Sep. 12, 2006 in U.S. Appl. No. 10/681,018, filed Oct. 3, 2006, 6 pages.

USPTO Restriction Requirement in U.S. Appl. No. 10/681,018, mailed Sep. 12, 2006, 5 pages.

USPTO Office Action in U.S. Appl. No. 11/555,697, mailed Aug. 3, 2009, 11 pages.

Kristina M. Grasso, ESQ. PLLC Amendment in Reply to Feb. 27, 2009 Final Office Action in U.S. Appl. No. 11/555,697, filed May 27, 2009, 12 pages.

USPTO Final Office Action in U.S. Appl. No. 11/555,697, mailed Feb. 27, 2009, 13 pages.

Kristina M. Grasso, ESQ. PLLC Amendment in Reply to Sep. 25, 2008 Notice of Non-Responsive Amendment in U.S. Appl. No. 11/555,697, filed Oct. 24, 2008, 7 pages.

USPTO Notice of Non-Responsive Amendment in U.S. Appl. No. 11/555,697, mailed Sep. 25, 2008, 2 pages.

Kristina M. Grasso, ESQ. PLLC Amendment in Reply to Mar. 28, 2008 Office Action in U.S. Appl. No. 11/555,697, filed Aug. 28, 2008, 10 pages.

USPTO Office Action in U.S. Appl. No. 11/555,697, mailed Mar. 28, 2008, 9 pages.

Kristina M. Grasso, ESQ. PLLC Amendment in Reply to Feb. 11, 2008 Notice of Non-Responsive Amendment in U.S. Appl. No. 11/555,697, filed Feb. 29, 2008, 4 pages.

USPTO Notice of Non-Responsive Amendment in U.S. Appl. No. 11/555,697, mailed Feb. 11, 2008, 2 pages.

Kristina M. Grasso, ESQ. PLLC Amendment in Reply to Oct. 17, 2007 Restriction Requirement in U.S. Appl. No. 11/555,697, filed Nov. 17, 2007, 6 pages.

USPTO Restriction Requirement in U.S. Appl. No. 11/555,697, mailed Oct. 17, 2007, 9 pages.

USPTO Office Action in U.S. Appl. No. 12/046,252, mailed Sep. 24, 2009, 11 pages.

USPTO Office Action in U.S. Appl. No. 11/232,180, mailed Nov. 25, 2009, 13 pages.

Kristina M. Grasso, ESQ. PLLC Amendment in Reply to Notice Non-Compliant Amendment dated Aug. 19, 2009 in U.S. Appl. No. 11/232,180, filed Aug. 19, 2009, 7 pages.
USPTO Notice Non-Compliant Amendment in U.S. Appl. No. 11/232,180, mailed Jun. 19, 2009, 2 pages.
Kristina M. Grasso, ESQ. PLLC Amendment in Reply to Mar. 13, 2009 Final Office Action in U.S. Appl. No. 11,232,180, filed Jun. 15, 2009, 12 pages.
USPTO Final Office Action in U.S. Appl. No. 11/232,180, mailed Mar. 13, 2009, 13 pages.
Kristina M. Grasso, ESQ. PLLC Response to Jan. 10, 2008 Restriction in U.S. Appl. No. 11/232,180, filed Mar. 3, 2008, 7 pages.
USPTO Restriction Requirement in U.S. Appl. No. 11/232,180, mailed Jan. 10, 2008, 6 pages.
Kristina M. Grasso, ESQ. PLLC Amendment in Reply to Notice Non-responsive Amendment dated Sep. 22, 2008 in U.S. Appl. No. 11/232,180, filed Oct. 20, 2008, 7 pages.
USPTO Notice Non-responsive Amendment in U.S. Appl. No. 11/232,180, mailed Sep. 22, 2008, 11 pages.
Kristina M. Grasso, ESQ. PLLC Amendment in Reply to Action dated Apr. 21, 2008 in U.S. Appl. No. 11/232,180, filed Aug. 21, 2008, 15 pages.
USPTO Office Action in U.S. Appl. No. 11/232,180, mailed Apr. 21, 2008, 9 pages.
Kristina M. Grasso, ESQ. PLLC Amendment in Reply to Restriction Requirement dated Jan. 10, 2008 in U.S. Appl. No. 11/232,180, filed Mar. 3, 2008, 7 pages.
USPTO Restriction Requirement in U.S. Appl. No. 11/232,180, mailed Jan. 10, 2008, 8 pages.
USPTO Office Action in U.S. Appl. No. 10/041,073, mailed Aug. 26, 2003, 7 pages.
USPTO Office Action in U.S. Appl. No. 10/730,567, mailed Dec. 19, 2005, 12 pages.
USPTO Office Action in U.S. Appl. No. 10/730,567, mailed Sep. 22, 2004, 3 pages.
USPTO Office Action in U.S. Appl. No. 10/730,567, mailed Jun. 30, 2004, 5 pages.
Office Action in U.S. Appl. No. 12/046,252, Sep. 24, 2009, 14 pages.
Kristina M. Grasso, ESQ. PLLC Preliminary Amendment in U.S. Appl. No. 12/046,252, filed May 18, 2009, 5 pages.
Kristina M. Grasso, ESQ. PLLC Amendment in Reply to Jun. 2, 2008 Notice of Non-Compliant Amendment in U.S. Appl. No. 12/046,252, filed Jul. 2, 2008, 5 pages.
U.S. Legal Instruments Examiner Tammy Acree Notice of Non-Compliant Amendment in U.S. Appl. No. 12/046,252, Jun. 2, 2008, 2 pages.
Restriction Requirement in U.S. Appl. No. 11/533,818 mailed Dec. 10, 2009, 9 pages.
Kristina M. Grasso, ESQ. PLLC Amendment in Reply to Jun. 25, 2007 Final Office Action filed Sep. 25, 2008, 9 pages.
Final Office Action in U.S. Appl. No. 11/213,255 mailed Jun. 25, 2008, 5 pages.
Kristina M. Grasso, ESQ. PLLC Amendment in Reply to Nov. 14, 2007 Office Action filed Mar. 4, 2008, 13 pages.
Office Action in U.S. Appl. No. 11/213,255 mailed Nov. 14, 2007, 2007, 8 pages.
Kristina M. Grasso, ESQ. PLLC Amendment in Reply to Jun. 22, 2007 Restriction Requirement filed Sep. 24, 2007, 7 pages.
Restriction Requirement in U.S. Appl. No. 11/213,255 mailed Jun. 22, 2007, 5 pages.
Maine & Asmus Response to May 7, 2007 Notice of Non-Compliant Amendment in U.S. Appl. No. 11/213,255, filed Jun. 7, 2007, 6 pages.
Notice of Non-Compliant Amendment in U.S. Appl. No. 11/213,255 mailed May 7, 2007, 2 pages.
USPTO Office Action in U.S. Appl. No. 11/213,382, mailed Mar. 25, 2008, 13 pages.
Kristina M. Grasso, ESQ. PLLC Amendment in Reply to Aug. 8, 2007 Office Action in U.S. Appl. No. 11/213,382, filed Dec. 12, 2007, 12 pages.
USPTO Office Action in U.S. Appl. No. 11/213,382, mailed Aug. 8, 2007, 9 pages.

Maine & Asmus Amendment in Reply to May 9, 2007 Restriction Requirement in U.S. Appl. No. 11/213,382, filed Jun. 8, 2007, 6 pages.
USPTO Restriction Requirement in U.S. Appl. No. 11/213,382, mailed May 9, 2007, 5 pages.
Authorized Officer S. Pilling, International Search Report in PCT/US2000/34000, mailed Jun. 29, 2001, 3 pages.
Authorized Officer P. Stienon, International Search Report in PCT/US2001/25343, mailed Mar. 11, 2002, 4 pages.
Authorized Officer Lee W. Young, International Search Report and the Written Opinion of the International Searching Authority in PCT/US0949374, mailed Sep. 25, 2009, 14 pages.
USPTO Office Action in U.S. Appl. No. 11/468,379 mailed Mar. 18, 2008, 15 pages.
USPTO Office Action in U.S. Appl. No. 10/041,037, mailed Aug. 26, 2003, 9 pages.
F. Chau & Associates, LLP Amendment in Reply to Aug. 23, 2004 Office Action dated Jul. 29, 2003 U.S. Appl. No. 10/041,037, filed Mar. 1, 2004, 11 pages.
Filipek et al., "The Screening and Diagnosis of Autistic Spectrum Disorders," *J Autism Dev Disord*, 1999, 29(6):439-484.
Happé and Frith, "The neuropsychology of autism," *Brain*, 1996, 119:1377-1400.
Munasinghe et al., "Digestive Enzyme Supplementation for Autism Spectrum Disorders: A Double-Blind Randomized Controlled Trial," *J Autism Dev Disord*, Mar. 5, 2010 [Epub ahead of print].
Perman et al., "Role of pH in Production of Hydrogen from Carbohydrates by Colonic Bacterial Flora. Studies In Vivo and In Vitro," *J Clin Invest*, 1981, 67:643-650.
Wohlman et al., "Enhancement of Drug Activity by Chymotrypsin, Penicillin Penetration into Granulomatous Lesions and Inflammatory Fluids," *Experientia*, 1969, 25(9):953-954.
Zhang et al., "Lactulose-Mannitol Intestinal Permeability Test in Children with Diarrhea Caused by Rotavirus and Cryptosporidium," *J Pediatric Gastroenterology Nutrition*, 2000, 31:16-21.
Fish & Richardson P.C., Amendment in Reply to Office Action in U.S. Appl. No. 10/681,018, filed Jun. 8, 2010, 16 pages.
Final Office Action in U.S. Appl. No. 11/555,697, mailed May 11, 2010, 21 pages.
Fish & Richardson P.C., Amendment in Reply to Office Action in U.S. Appl. No. 11/555,697, filed Feb. 3, 2010, 13 pages.
Final Office Action in U.S. Appl. No. 12/046,252, mailed Jul. 2, 2010, 28 pages.
Fish & Richardson P.C., Amendment in Reply to Office Action in U.S. Appl. No. 12/046,252, filed Mar. 24, 2010, 27 pages.
Office Action in U.S. Appl. No. 11/533,818 mailed Jul. 6, 2010, 26 pages.
Authorized Officer Lee W. Young, International Search Report/Written Opinion in PCT/US10/020259, mailed Mar. 5, 2010, 8 pages.
Authorized Officer Lee W. Young, International Search Report/Written Opinion in PCT/US10/020253, mailed Mar. 2, 2010, 9 pages.
Restriction Requirement in U.S. Appl. No. 12/283,090 mailed Oct. 7, 2009, 2 pages.
Fish & Richardson P.C., Amendment and Response in reply to Restriction Requirement in U.S. Appl. No. 12/283,090, filed Apr. 7, 2010, 9 pages.
Notice of Non-Compliant Amendment in U.S. Appl. No. 12/283,090, sent Apr. 27, 2010, 2 pages.
Fish & Richardson P.C., Response to Notice of Non-Compliance in U.S. Appl. No. 12/283,090, filed Apr. 29, 2010, 3 pages.
Fish & Richardson P.C., Supplemental Amendment and Response to Restriction Requirement in U.S. Appl. No. 12/283,090, filed Jun. 8, 2010, 8 pages.
Fish & Richardson P.C., Amendment and Response to Restriction Requirement in U.S. Appl. No. 12/487,868, filed Jun. 30, 2010, 42 pages.
Restriction Requirement in U.S. Appl. No. 12/487,868, mailed Jan. 13, 2010, 5 pages.
Office Action in U.S. Appl. No. 11/533,818 mailed Jul. 6, 2010, 26 pages.
Notice of Allowance dated Apr. 29, 2011 for U.S. Appl. No. 12/046,402.
Office Action dated Apr. 28, 2011 for U.S. Appl. No. 12/283,090.

Amendment dated Mar. 24, 2010 in Reply to Final Action dated Sep. 24, 2009 for U.S. Appl. No. 12/046,252.

Axcan Pharma Inc. Cdn Prescribing Information on VIOKASE Pancrelipase, USP tablets, powder. 2000: 1-3.

Dockter et al. Determination of chymotrypsin in the feces by a new photometric method. Padiatr Padol. 1985; 20(3):257-265.

Heijerman, et al. Omeprazole enhances the efficacy of pancreatin (pancrease) in cystic fibrosis. Ann Intern Med. Feb. 1, 1991; 114(3):200-1.

Kachrimanis, et al. Tensile strength and disintegration of tableted silicified microcrystalline cellulose: influences of interparticle bonding. J Pharm Sci. Jul. 2003;92(7):1489-501.

Marlicz et al. Determination of chymotrypsin in the stool in the diagnosis of chronic pancreatitis. Wiadomosci lekarskie. 1988; 41(11):704-707. (in Polish with English abstract/summary).

Mitchell, et al. Comparative trial of viokase, pancreatin and Pancrease pancrelipase (enteric coated beads) in the treatment of malabsorption in cystic fibrosis. Aust Paediatr J. Jun. 1982;18(2):114-7.

Notice of Allowance dated Apr. 15, 2011 for U.S. Appl. 12/487,868.
Office Action dated Mar. 29, 2011 for U.S. Appl. No. 12/054,343.
Office Action dated Mar. 30, 2011 for U.S. Appl. No. 12/786,739.

Levy, et al. Relationship of dietary intake to gastrointestinal symptoms in children with autistic spectrum disorders. Biol Psychiatry. Feb. 15, 2007;61(4):492-7.

Office Action dated Apr. 27, 2011 for U.S. Appl. No. 10/681,018.
Sturmey, Secretin is an ineffective treatment for pervasive developmental disabilities: a review of 15 double-blind randomized controlled trials. Res Dev Disabil. Jan.-Feb. 2005;26(1):87-97.

U.S. Appl. No. 13/002,136, filed Dec. 30, 2010, Fallon.
Brudnak et al. Enzyme-based therapy for autism spectrum disorders—is it worth another look? Med Hypoth. 2002; 58:422-428.
Final Office Action dated Feb. 14, 2011 for U.S. Appl. No. 12/049,613.

Hendren et al. Mechanistic biomarkers for autism treatment. Medical Hypotheses. 2009; 73:950-954.

International search report and written opinion dated Jan. 18, 2011 for PCT/US2010/057341.
International search report and written opinion dated Feb. 15, 2011 for PCT/US2010/053484.
International search report and written opinion dated Jun. 9, 2010 for PCT/US2010/030895.

Lieberman. Pharmaceutical Dosage Forms. vol. 2: Disperse Systems. New York Marcel Dekker, Inc. 1996; 243-258.

Lipase 30, Technical Data sheet, 1 page, Scientific Protein Laboratories LLC Jun. 13, 2005.

Office Action dated Jan. 21, 2011 for U.S. Appl. No. 12/386,051.
Office Action dated Oct. 1, 2001 for U.S. Appl. No. 09/466,559.
Office Action dated Oct. 5, 2010 for U.S. Appl. No. 12/046,402.
Office Action dated Nov. 15, 2010 for U.S. Appl. No. 12/238,415.
Office Action dated Apr. 22, 2003 for U.S. Appl. No. 09/929,592.
Office Action dated Jul. 22, 2010 for U.S. Appl. No. 12/049,613.
Office Action dated Aug. 13, 2002 for U.S. Appl. No. 09/929,592.
Office Action dated Aug. 20, 2010 for U.S. Appl. No. 12/283,090.
Office Action dated Aug. 25, 2010 for U.S. Appl. No. 12/487,868.

Pancreatic Enzyme Concentrate (PEC) Undiluted, Technical Data Sheet. 1 page, Scientific Protein Laboratories LLC Jun. 13, 2005.

Pancreatin 4X USP, Technical Data Sheet, 1 page, Scientific Protein laboratories LLC Jun. 13, 2005.

Schreck et al. Food preferences and factors influencing food selectivity for children with autism spectrum disorders. Res Develop Disabil. 2006; 27:353-363.

Stein, et a. Nitrogen Metabolism in normal and hyperkinetic boys, Am J Clin Nutr. 1984; 39:520-524.

USP (32)-NF(27) 2009, Pancreatin, V.3, pp. 3194-3195.

Wender et al. Prevalence of attention deficit disorder, residual type, and other psychiatric disorders in patients with irritable colon syndrome. Am J Psychiatry. 1983; 140(12):1579-82. Abstract only.

Ang, et al. Biological role and regulation of the universally conserved heat shock proteins, J Biol Chem, Dec. 25, 1991; 266(36):24233-6.

Arribas, et al. A comparative study of the chymotrypsia-like activity of the rat liver multicatalytic proteinase and the ClpP from *Escherichia coli*, J Biol Chem. Oct. 5, 1993; 268(28):211165-71.

Arrigo, et al. Expression of heat shock proteins during development in Drosophila. Results Probl Cell Differ. 1991;17:106-19.

Austic. Development and adaptation of protein digestion. J Nutr. May 1985;115(5):686-97.

Awazuhara, et al. Antifenicity of the proteins in soy lecithin and soy oil in soybean allergy, Clin Exp Allergy, Dec. 1998;28(12):1559-64.

Beilmann, et al. Neoexpression of the c-met/hepatocyte growth factor-scatter factor receptor gene in activated monocytes. Blood. Dec. 1, 1997;90(11);4450-8.

Borowitz, et al. Use of pancreatic enzyme supplements for patients with cystic fibrosis in the context of fibrosing colonopathy. Consensus Committee, J Pediatr, Nov. 1995;127(5):681-4.

Boyd, et al. Positively charged amino acid residue can act as toptgenic determinants in membrane proteins. proc Natl Acad Sci U S A. Dec. 1989;86(23);9446-50.

Bruhat, et al. Amino acid limitation induces expressin of CHOP, a CCAAT/enhancer binding protein-related geen, at both transcriptional and post-transcriptional levels, J Biol Chem. Jul. 11, 1997;272(28):17588-93.

Carroccio, et al. Secondary impairment of pancreatic function as a cause of severe malabsorption in intestinal giardiasis; a cause report. Am J Trop Med Hyg. Jun. 1997;56(6):599-602.

Carroccio, et al. Secretin-cerlein test and fecal chymotrypsin concentration in children with intestinal giardiasis. Int J Pancreatol. Oct. 1993;14(2):175-80.

Cassidy, et al. A new concept for the mechanism of action of chyrmotrypsin; the role of the low-barrier hydrogen bond, Biochemistry, Apr. 15, 1997;36(15);4576-84.

Chen, et al. Identification of two lysosomal membrane glyeoproteins J Cell Biol, Jul. 1985;101(1):85-95.

Corring, et al. Developmentt of digestive enzymes in the piglet from birth to 8 weeks. I. Pancreas and pancreatic enzymes. Nutr Metab, 1978;22(4)231-43.

Couet, et al. Identification of pptide and protein ligands for the caveolin-scaffolding domain. Implications for the interaction of caveolin with caveolae-associated proteins. J Biol Chem. Mar 7, 1997;272(10): 6525-33.

Craig, et al. Heat shock proteins: molecular chaperones of protein biogenesis. Microbiol Rev. Jun. 1993;57(2):402-14.

Croonenberghs, et al. Peripheral merkers of serotonergic and noradrenergic function in post-pubertal, caucasian males with autistic disorder. Nenropsychopharmacology, Mar. 2000;22(3):275-83.

Edelson, et al. 3-Cyclohexene-1-glycine, an Isoleucine Antagonist, J. Am. Chem. Soc, 1958; 80(11):2696-2700.

Ethridge, et al. Acute pancreatitis results in induction of heat shock proteins 70 and 27 and heat shock factor-1. Pancreas. Oct. 2000;21(3):248-56.

Fafournoux, et al. Amino acid regulation of gene expression. Biochem J. Oct. 1, 2000;351(Pt 1):1-12.

Fallingborg, et al. Measurement of gastrointestinal pH and regional transit times in normal children. J Padiatr Gastroenterol Nutr. Aug. 1990;11(2):211-4.

Fitzsimmons, et al. High-dose pancreatic-enzyme supplements and fibrosing colonopathy in children with cystic fibrosis, N. Engl J Med. May 1, 1997;336(18):1283-9.

Gardner. Absorption of inact peptides: studies on transport of protein digest and dipeptides across rat small intestine in vitro. Q J Exp Physiol. Oct. 1982;67(4):629-37.

Gardner Jr, et al. Porcine Pancreatic Lipase-A Glycoprotein, J Biol Chem. Jan. 1972;247(2):561-5.

Giglio, et al. Faailure to thrive: the earliest feature of cystic fibrosis in infants diagnosed by neonatal screening. Acta Paediatr. Nov. 1997;86(11)1162-5.

Goff, et al. Production of abnormal proteins in *E. coli* stimulates transcription of Ion and other heat shock genes, Cell. Jun. 1985;41(2);587-95.

Green, et al. Amino-terminal polymorphisms of the humn beta 2-adrenergic receptor impact distinct agonist-promoted regulatory properties. Biochemistry. Aug. 16, 1994;33(32):9414-9.

Gupta, et al. Th1- and Th2-like cytokines in CD4+ and CD8+ T cells in autism. J Neuroimmunol. May 1, 1998;85(1):106-9.

Hadjivassiliou, et al. Des cryptic gluten sensitivity play a part in neurological illness? Lancet, Feb. 10, 1996; 347(8998)369-71.

Horvath, et al, Gastrointestinal abnormalities in children with autistic disorder. J Pediatr, Nov. 1999;135(5):559-63.

Huang, et al. Apoptotic cell death in mouse models of GM2 gangliosidosis and observation on human Tay-Sachs and Sandhoff diseases. Hum Mol Genet, Oct. 1997(11):1879-85.

Huang, et al. Mapping of the human APOB gene to chromosome 2p and demonstration of a two-allele restriction fragment length polymorphisms. Proc Natl Acad Sci U S A, Feb. 1986;83(3):644-8.

Juhl, Fibromyalgia and the serotonin pathway. Altern Med Rev. 1998;3(5):367-375.

Koller, et al. Falls and Parkinson's Disease (Abstract). Clin Neuropharmacol. 1989;12(2):98-105.

Lloyd, Lysosome membrane permeability: implications for drug delivery. Adv Drug Deliv Rev. Mar. 30, 2000;41(2):189-200.

Luedtke, et al. Cathepsin A is expressed in a cell- and region-specific manner in the testis and epididymis and is not regulated y testicular or pitutary factors. J Histochem Cytochem, Aug. 2000;48(8):1131-46.

Mannino, et al. Surveillance for asthma—United States, 1960-1995, MMWR CDC Surveill Summ. Apr. 24, 1998;47(1):1-27.

McCormack, et al. Localization of the disulfide bond involved in post-transtational processing of glycosylasparaginase and disrupted by a mutation in the Finnish-type Aspartylglycosaminuria, J Biol Chem, Feb. 17, 1995;270(7):3212-5.

Melmed, et al., Metabolic markers and gastrointestinal symptoms in children with autism and related disorders, J Pediatr Gast Nutr. 2000; 31:S31-S32.

Mononen, et al. Aspartylglycosamimuria in the Finnish population: identification of two point mutations in the heavy chain of glycoasparaginase, Proc Natl Acad. Sci U S A. 1Apr. 1, 1991;88(7):2941-5.

Neuer, et al. The role of heat shock proteins in reproduction. Hum Reprod Update. Mar.-Apr. 2000;6(2)149-59.

Office Action dated May 24, 2011 for U.S. Appl. No. 12/487,864.

Puri, et al. Isolated segmental duodenal ganglionosis, Indian Journal of Radiology and Imaging, 2000;153-154.

Rider, et al. Perspective of biochernical research in the neuronal ceroid-lipofuscinosis. Am J Med Genet, Feb. 15, 1992;42(4):519-24.

Rottier, et al. Lack of PPCA expression only partially coincides with lysosomal storage in galactosialidosis mice: indirect evidence for spatial requirement of the catalytic rather that the protective function of PPCA. Hum MOl Genet. Oct. 1998;7(11):1787-94.

Sabra, et al. Linkage of ileal-lymphoid-nodular hyperplasia (ILNH), food allergy and CNS developmental: evidence for a non-IgE association. Ann Aller Asth Immunol, 1999;82-8.

Sandler, et al. Lack of benefit of a single dose of synthetic human secretin in the treatment of autism and pervasive developmental disorder. N Engl J Med, Dec. 9, 1999;341(24):1801-6.

Schafer, et al. Stress kinases and heat shock proteins in the pancreas; possible roles in normal function and disease., J Gastroenterol, 2000;35(1):1-9.

Singh, et al. Plasma increase of interleukin-12 and interferon-gamma Pathological significance in autism. J Neuroimmunol. May 1996;66(1-2):143-5.

Stein, et al. Nitrogen metabolism in normal and hyperkinetic boys, Am J Clin Nutr, Apr. 1984;39(4):520-4.

Steinherz, et al. Patterns of amino acid efflux from isolated normal and cystinotic human leucocyte lysosomes. J Biol Chem. Jun. 10, 1992;257(11):6041-9.

Stoll, at al. Enteral nutrient intake level determines intestinal protein synthesis and accretion rates in neonatal pigs. Am J Physiol Gastointest Liver Physiol. Aug. 2000;279(2):G288-94.

Strader, et al. Publication Structural basis of β-adrenergic receptor function. FASEB J. May 1989; 3(7):1825-32. 23-32, Thomas, at al. Defective protein frAding as a basis ofhoman ti,iseitse, Trends Biochem Se.d, 1995 Nov:20(1 0;456-9,.

Thomas, et al. Defective protein folding as a basis of human, Trends Biochem Sci, Nov. 1995;:20(11):456-9.

Vilanova, et al. Preparative isolation of the two forms of pig pancreatic pro-(carboxypeptidase A) and their monomeric carboxypeptidases A. Biochem J. Aug. 1, 1985;229(3):605-9.

Volkmar, et al. Practice parameters for the assessment. and treatment of children adolescents, and adults with autism and other pervasive developmental disorders. American Academy of Child and Adolescent Psychiarty Working Group on Quality Issues. J Am Acad Child Adolesc Psychiatry, (PART 1) Dec. 1999;38(12 Suppl):32S-54S.

Volkmar, et al. Practice Parameters for the Assessment and Treatment of Children, Adolescents, and Adults with Autism and other Pervasive Developmental, Disorders. American Academy of Child and Adolescent Psychiatry J Am Acad Child Adolesc Psychiatry (PART 2) Dec. 1999,38(12):1611-6.

Wakefield, et al. Enterocolitis in children with developmental disorders, Am J Gastroenterol. Sep. 2000:95(9):2285-95.

Wakefield, et al. Ileal-lymphoid-nodular hyperplasia, non-specific colitis; and pervasive developmental disorder in children. Lancet. Feb. 28, 1998;351(9103):637-41.

Walsh, et al. Heat shock and the role of the HSPs during neural plate induction in early mammalian CNS and brain development, Cell Mol Life Sci. Feb. 1997:53(2):198- 211.

Weintraub, et al. Morphometric studies of panereatic acinar granule formation in NCTR-Balb/c mice, J Cell Sci, May 1992;102 ( Pt 1):141-7.

Williams, et al, Eating habits of children with autism, Pediatr Nurs. May- Jan. 2000;26(3);259-64.

Youngberg, et al. Comparison of gastrointestinal pH in cystic fibrosis and healthy subjects, Dig Dis Sci. May 1987;32(5);472-80.

Yuan, et al., Freeze-Thaw Stability of Three Waxy Maize Staub Pastes Measured by Centrifugation and Calorimetry, Cereal Chem, 1998; 75(4)571-573.

Zeiner, et al. Mammalian protein RAP46: an interaction partner and modulator of 70 kDa beat shock proteins, EMBO J. Sep. 15, 1997;16(18);5483-90.

Cichoke, et al. The complete book of enzyme therapy. Penguin, 1998:39, 42, 47, 50, and 53.

Office action dated Jun. 29, 2011 for U.S. Appl. No. 11/555,697.

Notice of Allowance dated Jun. 27, 2011 for U.S. Appl. No. 12/238,415.

Notice of Allowance dated Jun. 28, 2011 for U.S. Appl. No. 12/487,868.

Notice of Allowance dated Jul. 8, 2011 for U.S. Appl. No. 12/046,402.

Derwent. Abstract for RU 2286785 Nov. 10, 2006. Downloaded from the Derwent file Jul. 13, 2011.

Notice of Allowance dated Aug. 8, 2011 for U.S. Appl. No. 12/426,794.

Smith, et al. Fecal chymotrypsin and trypsin determinations: Canadian Medical Association Journal. 1973;104(8):691-4 and 697.

* cited by examiner

| CHILD 1 | + H. pylori |
| | + Giardia |
| | + Cryptosporidium |
| | |
| CHILD 2 | + Rotavirus |
| | + Cryptosporidium |
| | + H. pylori |
| | + Girdia |

FIG. 1

| PATIENT | H.pylori | Cryptosporidium | E.histolytica | Giardia | Rota/virus | Camphylobacter | C. difficile |
|---|---|---|---|---|---|---|---|
| Parkinson 1 | ± | + | + | + | + | + | + |
| Parkinson 2 | + | + | + | + |  | + | + |
| Parkinson 3 | + |  |  | + | + | + |  |
| Parkinson 4 |  | + |  |  |  |  |  |
| Parkinson 5 | + | + |  |  | + |  |  |
| Parkinson 6 | + |  |  |  |  |  | + |
| Parkinson 7 | + |  | + | + |  |  |  |
| Parkinson 8 | + | + | + | + |  | + |  |
| Parkinson 9 |  | + |  | + | + | + | + |
| Parkinson 10 | + | + |  |  | + |  | + |
| Parkinson 11 | + |  |  |  | + |  | + |
| Parkinson 12 | + |  |  | + | + |  |  |
| Parkinson 13 |  | + | + | + |  | + |  |
| Parkinson 14 | + | + |  | + |  | + | + |
| Parkinson 15 | + | + |  |  | + | + |  |
| Non-P 1 |  |  |  |  |  |  |  |
| Non-P 2 |  |  |  |  |  |  |  |
| Non-P 3 |  |  |  |  |  |  |  |
| Non-P 4 |  |  |  |  |  |  |  |
| Non-P 5 |  |  |  |  |  |  |  |
| Non-P 6 |  |  |  | + |  |  |  |
| Non-P 7 |  |  |  |  |  |  |  |
| Non-P 8 |  |  |  |  |  |  |  |
| Non-P 9 |  |  |  |  |  |  |  |
| Non-P 10 |  |  |  |  |  |  |  |
| Non-P 11 |  |  |  |  |  |  |  |
| Non-P 12 | + |  |  |  |  |  |  |
| Non-P 13 |  |  |  |  |  |  |  |
| Non-P 14 |  |  |  |  |  |  |  |
| Non-P 15 |  |  |  |  |  |  |  |

FIG. 2

| PATIENT | Age | H.pylori | Cryptosporidium | E.histolytica | Giardia | Rotavirus | Camphylobacter | C.difficile |
|---|---|---|---|---|---|---|---|---|
| ADD 1 | 10 | + | | + | + | + | | + |
| ADD 2 | 6 | + | + | | | | | + |
| ADHD 3 | 9 | | | + | | + | + | |
| ADHD 4 | 6 | | + | + | + | | + | |
| ADD 5 | 9 | + | + | + | + | + | + | + |
| ADD 6 | 11 | | + | | | | + | |
| ADD 7 | 14 | + | | | | + | | |
| ADHD 8 | 4 | + | + | + | | | | |
| ADD 9 | 16 | | + | + | + | + | + | |
| ADHD 10 | 12 | | + | + | | | | + |
| ADD 11 | 11 | + | | | | + | + | |
| ADD 12 | 7 | | + | | + | + | | + |
| ADD 13 | 9 | + | + | + | + | | + | |
| | | | | | | | | |
| Non-ADD 1 | 10 | | | | | | | |
| Non-ADD 2 | 6 | | | + | | | | |
| Non-ADD 3 | 9 | | | | | | | |
| Non-ADD 4 | 6 | | | | | | | |
| Non-ADD 5 | 9 | | | | | | | |
| Non-ADD 6 | 11 | + | | | | | + | |
| Non-ADD 7 | 14 | | | | | | | |
| Non-ADD 8 | 4 | | | | | | | |
| Non-ADD 9 | 16 | | | | | | | |
| Non-ADD 10 | 12 | | | | | | | |
| Non-ADD 11 | 11 | + | | | | | | |
| Non-ADD 12 | 7 | | | | | | | |
| Non-ADD 13 | 9 | | | | | | | |
| Non-ADD 14 | 9 | | | | | | | |

FIG. 3

| Patient | Giardia | Cryptosporidium | E.Histolytica | Adendovirus | Rotavirus | H.Pylori | Cyclospora | Mycrosporidia | IsosporaBelh |
|---|---|---|---|---|---|---|---|---|---|
| Autistic 1 | + | | | | | | | | + |
| Autistic 2 | | + | | | | + | | | |
| Autistic 3 | + | | | | | + | | | |
| Autistic 4 | | | | + | | + | | | |
| Autistic 5 | + | | | | | | | | |
| Autistic 6 | | + | | | + | | | | |
| Autistic 7 | + | | | | | + | | | |
| NonAutistic1 | | | | | | | | | |
| NonAutistic2 | | | | | | | | | |
| NonAutistic3 | | | | | | | | | |
| NonAutistic4 | | | | | | | | | |
| NonAutistic5 | | | | | | | | | |
| NonAutistic6 | | | | | | | | | |
| NonAutistic7 | | | | | | | | | |

FIG. 4

METHODS FOR DIAGNOSING PERVASIVE DEVELOPMENT DISORDERS, DYSAUTONOMIA AND OTHER NEUROLOGICAL CONDITIONS

CROSS REFERENCE TO RELATED APPLICATION

This application is based on, and claims the benefit of, U.S. Provisional Application No. 60/249,239, filed on Nov. 16, 2000, which is fully incorporated herein by reference.

TECHNICAL FIELD OF THE INVENTION

The present invention generally relates to methods for aiding in the diagnosis of disorders including, but not limited to, PDDs (Pervasive Development Disorders), Dysautonomic disorders, Parkinsons disease and SIDS (Sudden Infant Death Syndrome). More particularly, the invention relates to a diagnosis method comprising analyzing a stool sample of an individual for the presence of a biological marker (or marker compound) comprising one or more pathogens, which provides an indication of whether the individual has, or can develop, a disorder including, but not limited to, a PDD, a Dysautonomic disorder, Parkinson's disease or SIDS.

BACKGROUND

Currently, extensive research is being conducted to determine associations between gastrointestinal dysfunction and a variety of human disorders that, heretofore, have been of unknown etiology. For example, an association between dysautonomic conditions and gastrointestinal dysfunction has been described in U.S. patent application Ser. No. 09/929,592, filed on Aug. 14, 2001, entitled "Methods For Diagnosing and Treating Dysautonomia and Other Dysautonomic Conditions, which is commonly owned and fully incorporated herein by reference. Further, a relationship between gastrointestinal conditions and PDDs such as Autism, ADD (Attention Deficit Disorder) and ADHD (Attention Deficit Hyperactivity Disorder) has been described in detail in U.S. patent application Ser. No. 09/466,559, filed Dec. 17, 1999, entitled "Methods For Treating Pervasive Development Disorders," and U.S. Ser. No. 09/707,395, filed on Nov. 7, 2000, entitled "Methods For Treating Pervasive Development Disorders", both of which are commonly owned and incorporated herein by reference.

U.S. patent application Ser. No. 09/466,559 (now U.S. Pat. No. 6,534,063) and U.S. patent application Ser. No. 09/707,395 (now U.S. Pat. No. 6,632,429) relate generally to a method for treating individuals diagnosed with a form of PDD (pervasive development disorder) and other disorders such as ADD (attention deficit disorder) and ADHD (attention deficit hyperactivity disorder). More specifically, the present invention is directed to therapeutic methods for treating individuals with such disorders by administering secretin, other neuropeptides, peptides, and/or digestive enzymes, as well as a prognosticative method for determining the potential effectiveness of the administration of secretin, other neuropeptides, peptides, and/or digestive enzymes for the treatment of such disorders. The spectrum of PDDs include disorders such as Autism, Aspergers, ADD, and ADHD. PDDs are typically characterized by multiple distortions in the development of basic psychological functions that are involved in the development of social skills and language, such as attention, perception reality testing and motor movement. In addition, many children diagnosed with Autism, for example, suffer from primary diffuse gastrointestinal problems such as protracted diarrhea and constipation.

The invention involves determining the presence of abnormal protein digestion of individuals, especially children, by measuring the chymotrypsin levels so as to determine if the individual is likely to benefit from the administration of secretin, digestive enzymes, peptides and/or neuropeptides. Tests were performed to measure the fecal chymotrypsin levels (referred to herein as Fecal Chymotrypsin Test) in children who span the entire PDD spectrum and whose symptomotology place them in this DSM IV category. Such tests revealed that a majority of the children diagnosed with autism, ADD and ADHD, for example, had abnormal chymotrypsin levels. Those children having abnormal levels of chymotrypsin in their stools are considered candidates for secretin administration. Other factors that may be considered in determining which children are potential candidates for secretin administration aside from the fecal chymotrypsin levels include a previously diagnosed history of autism, a history of gastrointestinal (GI) dysfunction, including any history of protracted diarrhea or constipation lasting for a weeks or months, as well as a self-limiting diet consisting primarily of carbohydrates. Upon determining that a given child was likely to benefit from secretin administration based on the results of the fecal chymotrypsin test, the child was administered a CARS (Childhood Autism Rating Scale) test prior to being scheduled for secretin infusion.

Another experiment was performed to determine the effect of the administration of digestive enzymes to Autistic children. Each of the 17 autistic children were administered digestive/pancreatic enzymes comprising amylases, proteases, lipases, sucrases, maltases, and other digestive/pancreatic enzymes including trypsin and chymotrypsin. The measured fecal chymotrypsin levels of at least 16 of the 17 autistic children were found to increase 6 months post-digestive enzyme administration. Furthermore, a notable decrease in autistic symptomotology of each of the 17 autistic children was observed as a result of digestive/pancreatic enzyme administration.

Based on these findings, it is thus desirable to continue research in finding biologic markers of gastrointestinal dysfunction that may aid in the diagnosis of certain diseases and disorders. For example, the effect of various pathogens on the gastrointestinal tract, and the association of such pathogens to disorders such as PDD and dysautonomia, has heretofore not been researched. Various microorganisms that are of interest will now be discussed.

*Helicobacter pylori* (*H. pylori*) is generally associated with chronic gastritis and peptic ulcer in children and adults. The prevalence of *H. pylori* is highest in developing countries and lowest in developed countries. Ethnicity, socioeconomic status, household crowding, and other conditions contribute to the formation of *H. pylori* infection. Infection is rarely symptomatic in children, and duodenal ulcers are generally not seen in children less than 10 years of age. Various diseases that are caused, or believed to be caused by *H. pylori* infection are known. For instance, it has been postulated that *H. pylori* plays a role in auto-immune athero-sclerosis.

Esophageal reflux disease (GORD) has further been postulated to be caused by *H. pylori* in a mechanism whereby somatostatin induces the hypothalamus to decrease the release of growth hormone from the pituitary affecting the adrenal control of cortisol. The change in cortisol ultimately affects the gastrin release mechanism causing an increase in acid.

*Cryptosporidium parvum* can be associated with infections of the gastrointestinal tract in children and in immunocompromised populations. It is generally thought to account for up to 20% of all cases of diarrhea in developing countries and potentially life threatening in children with AIDS due to the induction of severe malnutrition. These infections are generally asymptomatic and occur in tandem with other infections such as one with *Giardia*.

In 1993, a large outbreak of *Cryptosporidium parvum* occurred in Milwaukee Wis. in which 400,000 people were affected. It has a seasonal effect of being more prevalent in the late summer in children under the age of 15 years.

*Giardia lamblia* is a common cause of diarrhea in humans and other mammals throughout the world. In its most severe form, it has been found to cause infectious lymphocytosis. Although rare, infection with *Giardia* can be protracted and debilitating. *Giardia lamblia* is a flagellate that encysts, and generally does not cause symptomotology. However, when found in the trophozoite form, severe diarrhea can result. Symptoms can include diarrhea, vomiting, fatigue, and growth retardation in children. Malabsorption results from infection with the trophzoite form, and potential blockage of the microvilli of the intestines occurs. There may be an interaction between decreased levels of IgA in the gastrointestinal system and giardiasis.

*Clostridium* infections of the gastrointestinal tract are of the *perfringes, botulinum* and *difficile* varieties. Perfringens food poisoning is the term used to describe the common foodborne illness caused by *C. perfringens*. A more serious but rare illness is also caused by ingesting food contaminated with Type C strains. The latter illness is known as enteritis necroticans. The common form of perfringens poisoning is characterized by intense abdominal cramps and diarrhea which begin 8-22 hours after consumption of foods containing large numbers of those *C. perfringens* bacteria capable of producing the food poisoning toxin. The illness is usually over within 24 hours but less severe symptoms may persist in some individuals for 1 or 2 weeks. A few deaths have been reported as a result of dehydration and other complications. Necrotic enteritis caused by *C. perfringens* is often fatal. This disease also begins as a result of ingesting large numbers of the causative bacteria in contaminated foods. This disease is a food infection; only one episode has ever implied the possibility of intoxication (i.e., disease from preformed toxin).

*Clostridium difficile* is an infection generally caused by changes in the intestinal mucosa. Those changes are caused by an overuse of antibiotics creating an intestinal environment favorable to the infiltration with *Clostridium difficile*. Infection with *C. difficile* is generally debilitating and *C. difficile* is a gram-positive, spore forming, anaerobic bacillus which can produce toxin-mediated diarrhea or pseudomembranous colitis. It has been isolated from soil, sand, hay, and animal dung. *C. difficile* colonization of the colon occurs in 2%-3% of healthy adults. Following exposure to antibacterial agents, the rate of asymptomatic colonization in adults averages between 5% to 15%, but rates as high as 46% have been reported. Carriage rates of up to 70% have been reported in children below the age of one year, but by two years of age the "normal" colonic flora is established and the frequency of colonization decreases to that of healthy adults. Of interest is that healthy children less than one year of age are the only population in which *C. difficile* toxins are frequently detected in the stool in the absence of clinical symptoms. One suggestion advanced to explain this observation is that the infant's gut cannot respond to the toxin.

*Clostridium botulinum* is an anaerobic, spore-forming rod that produces a potent neurotoxin. The spores are heat-resistant and can survive in foods that are incorrectly or minimally processed. Seven types (A, B, C, D, E, F and G) of botulism are recognized, based on the antigenic specificity of the toxin produced by each strain. Types A, B, E and F cause human botulism. Types C and D cause most cases of botulism in animals. Animals most commonly affected are wild fowl and poultry, cattle, horses and some species of fish. Although type G has been isolated from soil in Argentina, no outbreaks involving it have been recognized. Foodborne botulism (as distinct from wound botulism and infant botulism) is a severe type of food poisoning caused by the ingestion of foods containing the potent neurotoxin formed during growth of the organism. The toxin is heat labile and can be destroyed if heated at 80° C. for 10 minutes or longer. The incidence of the disease is low, but the disease is of considerable concern because of its high mortality rate if not treated immediately and properly. Most of the 10 to 30 outbreaks that are reported annually in the United States are associated with inadequately processed, home-canned foods, but occasionally commercially produced foods have been involved in outbreaks. Sausages, meat products, canned vegetables and seafood products have been the most frequent vehicles for human botulism.

The life cycle of *Entamoeba histolytica* involves trophozoites (the feeding stage of the parasite) that live in the host's large intestine and cysts that are passed in the host's feces. Humans are infected by ingesting cysts, most often via food or water contaminated with human fecal material. The trophozoites can destroy the tissues that line the host's large intestine, so of the amoebae infecting the human gastrointestinal tract, *E. histolytica* is potentially the most pathogenic. In most infected humans the symptoms of "amoebiasis" (or "amebiasis") are intermittent and mild (various gastrointestinal upsets, including colitis and diarrhea). In more severe cases the gastrointestinal tract hemorrhages, resulting in dysentery. In some cases the trophozoites will enter the circulatory system and infect other organs, most often the liver (hepatic amoebiasis), or they may penetrate the gastrointestinal tract resulting in acute peritonitis; such cases are often fatal. As with most of the amoebae, infections of *E. histolytica* are often diagnosed by demonstrating cysts or trophozoites in a stool sample. Infections that sometimes last for years may be accompanied by no symptoms, vague gastrointestinal distress, and/or dysentery (with blood and mucus). Most infections occur in the digestive tract but other tissues may be invaded. Complications include ulcerative and abscess pain and, rarely, intestinal blockage. Onset time is highly variable. It is theorized that the absence of symptoms or their intensity varies with such factors as strain of amoeba, immune health of the host, and associated bacteria and, perhaps, viruses. The amoeba's enzymes help it to penetrate and digest human tissues; it secretes toxic substances.

No extensive research is known to have been conducted heretofore to determine correlations and associations regarding the presence of pathogens in the gastrointestinal tract of individuals in, e.g., PDD, Parkinson's and Dysautonmia populations. Based on the findings described herein in accordance with the present invention, correlations and associations are found to exist between various disorders such as Autism, Parkinson's, ADD, ADHD and Dysautonomia, for example, and the presence of pathogens in an individual's digestive tract.

SUMMARY OF THE INVENTION

The present invention generally relates to methods for aiding in the diagnosis of disorders including, but not limited to, PDDs, Dysautonomic disorders, Parkinson's disease and SIDS. More particularly, the invention relates to a diagnosis method comprising analyzing a stool sample of an individual for the presence of a biological marker comprising one or more pathogens, which provides an indication of whether the individual has, or can develop, a disorder including, but not limited to, a PDD, Dysautonomia, Parkinson's disease and SIDS. In a preferred embodiment, a stool immunoassay is used to determine the presence of antigens in a stool sample, wherein such antigens are associated with one or more pathogens including, but not limited to, *Giardia, Cryptosporidium, E. histolytica, C. difficile*, Adenovirus, Rotavirus or *H. pylori*.

In another aspect of the invention, pathogens including, but not limited to, *Giardia, Cryptosporidium, E. histolytica, C. difficile*, Adenovirus, Rotavirus, and *H. pylori*, comprise biological markers whose presence in a stool sample, for example, are efficacious for determining whether an individual, especially a child, has, or can potentially develop, a disorder including, but not limited to, a PDD, Dysautonomia, Parkinsons disease, SID, and/or other neurological disorders.

These and other aspects, features, and advantages of the present invention will be described and become apparent from the following detailed description of preferred embodiments, which is to be read with the accompanying drawings.

BRIEF DESCRIPTION OF THE DRAWINGS

FIG. 1 is a table diagram illustrating various pathogens that tested positive in stool samples of individuals having a Dysautonomic disorder;

FIG. 2 is a table diagram illustrating various pathogens that tested positive in stool samples of individuals having Parkinson's, as compared with stool results of individuals not having Parkinson's disease;

FIG. 3 is a table diagram illustrating various pathogens that tested positive in stool samples of individuals having ADD or ADHD, as compared with stool results of individuals not having ADD or ADHD; and FIG. 4 is a table diagram illustrating various pathogens that tested positive in stool samples of individuals having a PDD.

DETAILED DESCRIPTION OF PREFERRED EMBODIMENTS

The present invention is directed to methods for aiding in the diagnosis of various human disorders, such as PDD, Dysautonomia, Parkinson's, SIDS, etc. In one aspect, a method comprises analyzing stool samples of an individual to determine the presence of pathogens including, but not limited to, *Giardia, Cryptosporidium, Entamoeba histolytica*, Adenovirus, Rotavirus, *H. pylori, Cyclospora, Microsporidia*, and/or *Isospora belli*. Preferably, the presence of one or more pathogens is determined using a stool immunoassay to determine the presence of antigens in a stool sample, wherein such antigens are associated with one or more pathogens including, but not limited to, *Giardia, Cryptosporidium, E. histolytica, C. difficile*, Adenovirus, Rotavirus or *H. pylori*.

In particular, a stool immunoassay results in the determination of the presence of a particular antigen (usually a protein) that the particular pathogen leaves behind (i.e., each microorganism is associated with a specific antigen). This antigen represents a pathogen, and is recognized by the gastrointestinal tract of the individual as a foreign protein. In accordance with one aspect of the invention, the presence of one or more antigens, regardless of the quantitative level, comprises a biological marker for determining if the person, especially a child, may either have or develop a disorder such as a PDD, Dysautonomia, Parkinson's, or SIDs.

Until now, there has been no known methods for analyzing stool samples to determine the presence of pathogens as biological markers to allow early diagnosis or screening of such disorders or conditions. It is postulated, for example, that the presence of antigen(s) and/or the microscopic presence of such organisms may signal the formation of a dysbiosis, and ultimately the formation of a malabsorption syndrome. This malabsorption syndrome can predispose the individual to the formation of a disorder such as autism, ADD, ADHD, SIDS, PDD, tourettes, OCD and other neurological conditions. In particular, the formation of malabsorption syndrome can affect, for instance, proper and essential protein digestion/absorption. And in the absence of proper protein digestion/absorption, the amino acids necessary for, e.g., the growth and development or normal functioning of certain chemical processes of individuals are absent.

Consequently, it is postulated, for example, that a lack of proper protein absorption, for instance, of an individual, especially children, can lead to various disorders such as autism, other PDDs, SIDS, and other disorders mentioned herein. Indeed, as described in each of the above-incorporated U.S. Patent Applications, abnormal protein digestion is found to occur in the PDD and dysautonomic populations. For instance, it was further determined that a sub-population of individuals suffering from ADD, ADHD and autism as well as a sub-population of those with dysautonomic conditions had an abnormal level of the enzyme chymotrypsin, indicated pancreatic insufficiency as a component of such disorders.

The following case studies indicate that there are correlations between the development of various disorders and the presence of microorganisms in an individual's digestive tract. It is to be understood that these examples are set forth by way of illustration only, and nothing therein shall be taken as a limitation upon the overall scope of the invention.

Case 1:

Stool sample were collected from two children diagnosed as having Familial Dysautonomia. The stool samples were analyzed for the presence of pathogens. As shown by the table in FIG. 1, the stool sample of Child 1 tested positive for *H. pylori, Giardia*, and *Cryptosporidium*. Further, the stool sample of Child 2 tested positive for *H. pylori, Giardia, Cryptosporidium* and Rotavirus.

Case 2:

Stool samples were collected from 15 individuals diagnosed as having Parkinson's disease. The stool samples were analyzed for the presence of pathogens. Further, stool samples were collected from an additional 15 individuals who were not diagnosed as having Parkinson's disease, nor having known familial association with Parkinson's or known GI conditions. These stool samples were also analyzed for the presence of pathogens.

The table in FIG. 2 illustrates the result of this study. As shown, the stools of each of the 15 individuals diagnosed as having Parkinson's disease tested positive for various pathogens including *H. pylori, Cryptosporidium, E. hystolytica, Giardia*, Rotavirus, *Camphylobacter*, and/or *C. difficile*. On the other hand, virtually all the stools of each of the 15 individuals not diagnosed as having Parkinson's disease tested negative for such pathogens.

Case 3:

Stool samples were collected from 13 children diagnosed as having either ADD or ADHD and analyzed for the presence of pathogens. Further, stool samples were collected from an additional 14 children not diagnosed as having ADD or ADHD and analyzed for the presence of pathogens.

The table in FIG. 3 illustrates the result of this study. As shown, the stools of each of the 13 children diagnosed as having either ADD or ADHD tested positive for various pathogens including as *H. pylori, Cryptosporidium, E. hystolytica, Giardia*, Rotavirus, *Camphylobacter*, and/or *C. difficile*. On the other hand, virtually all the stools of each of the 14 children not diagnosed as having ADD or ADHD tested negative for such pathogens.

Case 4:
Stool samples were collected from 7 children diagnosed as having Autism (via a CARS or ADOS test) and from 7 children not diagnosed as having Autism, and the stool samples were analyzed for the presence of pathogens including *Giardia, Cryptosporidium, Entamoeba histolytica*, Adendovirus, Rotavirus, *H. pylori, Cyclospora, Mycrosporidia* and *Isospora belli*, by means of immunoassay. The results of this study are shown in FIG. 4. As shown, the stools of each of the 7 children diagnosed as having Autism tested positive for various pathogens including *Giardia, Cryptosporidium*, Adendovirus, Rotavirus, *H. pylori*, and/or *Isospora belli*, whereas each of the 7 non-autistic children were tested negative for the presence of such pathogens.

The results of these case studies indicate that there are correlations between the development of various disorders (such as Autism, Parkinson's, ADD and ADHD) and the presence of pathogens and/or corresponding antigens in an individual's digestive tract. It is postulated that these pathogens and/or corresponding antigens either promote gastrointestinal dysfunction or have some other direct or indirect effect on the individual, thereby causing such disorders. Further, it is possible that certain mechanisms associated with such disorders can be the cause of a proliferation of one or more pathogens in the gastrointestinal tract of an individual. Again, it is to be understood that nothing therein shall be taken as a limitation upon the overall scope of the invention.

For instance, although Case Study 4 involves Autism, based on the correlations described herein, it is believed that the present invention may be implemented for aiding in the diagnosis of other various PDDs such as Aspergers syndrome and other related disorders. Furthermore, although Case Study 1 involves Familial Dysautonomia, based on the correlations described herein, it is believed that the present invention may be implemented for aiding in the diagnosis of various dysautonomic disorders and dysautonomic conditions, including, but not limited to, Familial Dysautonomia (or Riley-Day Syndrome), Guillaine-Barre Syndrome (GBS) (acute idiopathic polyneuropathy), fetal fatal insomnia (FFI), diabetic cardiovascular neuropathy, Hereditary Sensory and autonomic neuropathy type III (HSAN III), central autonomic disorders including multiple system atrophy (Shy-Drager syndrome), orthostatic intolerance syndrome including mitral value prolapse, postural tachycardia syndrome (POTS), and idiopathic hypovolemia, dysautonomic syndromes and disorders of the catecholemine family including baroreflex failure, dopamine-B-Hydroxylase deficiency, pheochromocytoma, chemodectina, familial paraganglioma syndrome, tetrahydrobiopterin deficiency, aromatic-L-amino acid decarboxylase deficiency, Menke's disease, monoamine oxidase deficiency states, and other disorders of dopamine metabolism, dysautonomic syndromes and disorders of the cardiovasular system, Chaga's disease, Diabetic autonomic failure, pure autonomic failure, syncope, hypertension, cardiovascular disease, renal disease and SIDS. Further, the present invention is believed to be efficacious for diagnosing other neurological disorders such as OCD (obsessive compulsive disorder) and Tourette's syndrome.

In summary, a method according to the present invention for aiding in the diagnosis of a disorder comprises analyzing stool samples of an individual to determine the presence of one or more pathogens including, but not limited to, *H. pylori, Cryptosporidium, Entamoeba histolytica, Giardia*, Rotavirus, *Camphylobacter*, and/or *C. difficile*. Other pathogens that may be analyzed include, for example, Adenovirus, *Cyclospora, Microsporidia*, and/or *Isospora belli*. In a preferred embodiment, the presence of one or more pathogens is determined by a stool immunoassay to determine the presence of associated antigens. The presence of one or more pathogens comprises a biological marker for determining if an individual, especially a child, may either have or develop a disorder, including, but not limited to, PDD (such as Autism), Dysautonomia (or other dysautonomic conditions), Parkinson's disease, SIDS, or other dysautonomic and/or neurological disorders.

Although illustrative embodiments have been described herein with reference to the accompanying drawings, it is to be understood that the present invention is not limited to those precise embodiments, and that various other changes and modifications may be effected therein by one skilled in the art without departing from the scope or spirit of the invention. All such changes and modifications are intended to be included within the scope of the invention as defined by the appended claims.

What is claimed is:

1. A method for screening an individual for risk of having or developing Autism, comprising the steps of:
    obtaining a stool sample from the individual;
    analyzing the stool sample to detect the presence or absence of one or more antigens associated with two or more pathogens, wherein the two or more pathogens comprise *Helicobacter pylori, Cryptosporidium, Entamoeba histolytica, Giardia*, Rotavirus, Adenovirus, *Cyclospora, Microsporidia*, or *Isospora belli;*
    analyzing the stool sample to detect the level of chymotrypsin present;
    determining that the individual is at risk of having or developing Autism based on the presence of the one or more antigens associated with the two or more pathogens and an abnormally low level of chymotrypsin in the stool sample.

2. The method of claim 1, wherein the step of analyzing comprises performing a stool immunoassay.

3. The method of claim 1, wherein at least one of the two or more pathogens is *Helicobacter pylori*.

4. The method of claim 1, wherein at least one of the two or more pathogens is *Cryptosporidium*.

5. The method of claim 1, wherein at least one of the two or more pathogens is *Entamoeba histolytica*.

6. The method of claim 1, wherein at least one of the two or more pathogens is *Giardia*.

7. The method of claim 1, wherein at least one of the two or more pathogens is Rotavirus.

8. The method of claim 1, wherein at least one of the two or more different pathogens is Adenovirus.

9. The method of claim 1, wherein at least one of the two or more different pathogens is *Cyclospora*.

10. A method for diagnosing an individual as having or likely to develop Autism, the method comprising:
    obtaining a stool sample from the individual;
    analyzing the stool sample to detect the presence or absence of one or more antigens associated with two or more pathogens, wherein the two or more pathogens comprise *Helicobacter pylori, Cryptosporidium, Entamoeba histolytica, Giardia*, Rotavirus, Adenovirus, *Cyclospora, Microsporidia*, or *Isospora Belli;* analyzing the stool sample to detect the level of chymotrypsin present; diagnosing the individual as having or likely to develop autism based on the presence of the one or more antigens associated with the two or more different pathogens and an abnormally low level of chymotrypsin in the stool sample.

11. The method of claim 10, wherein the step of analyzing comprises performing a stool immunoassay.

12. The method of claim 10, wherein at least one of the two or more pathogens is *Helicobacter pylori*.

13. The method of claim 10, wherein at least one of the two or more pathogens is *Cryptosporidium*.

14. The method of claim 10, wherein at least one of the two or more pathogens is *Entamoeba histolytica*.

15. The method of claim 10, wherein at least one of the two or more pathogens is *Giardia*.

16. The method of claim 10, wherein at least one of the two or more pathogens is Rotavirus.

17. The method of claim 10, wherein at least one of the two or more pathogens is Adenovirus.

18. The method of claim 10, wherein at least one of the one or more pathogens is *Cyclospora*.

19. The method of claim 2, wherein the stool immunoassay comprises detecting one or more polypeptide antigens associated with two or more-pathogens-wherein the two or more pathogens comprise *Helicobacter pylori, Cryptosporidium, Entamoeba histolytica, Giardia*, Rotavirus, Adenovirus, *Cyclospora, Microsporidia*, or *Isospora belli*.

20. The method of claim 11, wherein the stool immunoassay comprises detecting one or more polypeptide antigens associated with two or more-pathogens-wherein the two or more pathogens comprise *Helicobacter pylori, Cryptosporidium, Entamoeba histolytica, Giardia*, Rotavirus, Adenovirus, *Cyclospora, Microsporidia*, or *Isospora belli*.

21. A method of screening an individual for risk of developing Autism, the method comprising:
obtaining a stool sample from the individual;
analyzing the stool sample to detect the presence or absence of one or more antigens associated with two or more pathogens, wherein the two or more pathogens comprise *Helicobacter pylori, Cryptosporidium, Entamoeba histolytica, Giardia*, Rotavirus, Adenovirus, *Cyclospora, Microsporidia*, or *Isospora belli;*
analyzing the stool sample to detect the level of chymotrypsin present;
identifying the individual as having an increased risk of developing Autism based on the presence of the one or more antigens associated with the two or more different pathogens and an abnormally low level of chymotrypsin in the stool sample.

22. The method of claim 21, wherein the step of analyzing comprises performing a stool immunoassay.

23. The method of claim 21, wherein at least one of the two or more pathogens is *Helicobacter pylori*.

24. The method of claim 21, wherein at least one of the two or more pathogens is *Cryptosporidium*.

25. The method of claim 21, wherein at least one of the two or more pathogens is *Entamoeba histolytica*.

26. The method of claim 21, wherein at least one of the two or more pathogens is *Giardia*.

27. The method of claim 21, wherein at least one of the two or more pathogens is Rotavirus.

28. The method of claim 21, wherein at least one of the two or more pathogens is Adenovirus.

29. The method of claim 21, wherein at least one of the two or more pathogens is *Cyclospora*.

30. The method of claim 1, further comprising treating an individual determined to have Autism by administering one or more digestive enzymes comprising chymotrypsin.

31. The method of claim 10, further comprising treating an individual determined to have Autism by administering one or more digestive enzymes comprising chymotrypsin.

32. The method of claim 21, further comprising treating an individual determined to have Autism by administering one or more digestive enzymes comprising chymotrypsin.

33. The method of claim 1, wherein the individual exhibits one or more symptoms of Autism.

34. The method of claim 10, wherein the individual exhibits one or more symptoms of Autism.

35. The method of claim 21, wherein the individual further exhibits one or more symptoms of Autism.

36. The method of claim 30, wherein the digestive enzymes further comprise amylases, proteases, and lipases.

37. The method of claim 31, wherein the digestive enzymes further comprise amylases, proteases, and lipases.

38. The method of claim 32, wherein the digestive enzymes further comprise amylases, proteases, and lipases.

39. The method of claim 1, wherein at least one of the two or more pathogens is *Microsporidia*.

40. The method of claim 1, wherein at least one of the two or more pathogens is *Isospora belli*.

41. The method of claim 10, wherein at least one of the two or more pathogens is *Microsporidia*.

42. The method of claim 10, wherein at least one of the two or more pathogens is *Isospora belli*.

43. The method of claim 21, wherein at least one of the two or more pathogens is *Microsporidia*.

44. The method of claim 21, wherein at least one of the two or more pathogens is *Isospora belli*.

* * * * *